US00RE34705E

United States Patent [19]

Galibert et al.

[11] E Patent Number: Re. 34,705

[45] Reissued Date of Patent: Aug. 23, 1994

[54] NUCLEOTIDIC SEQUENCE CODING THE SURFACE ANTIGEN OF THE HEPATITIS B VIRUS, VECTOR CONTAINING SAID NUCLEOTIDIC SEQUENCE, PROCESS ALLOWING THE OBTENTION THEREOF AND ANTIGEN OBTAINED THEREBY

[75] Inventors: Francis Galibert, Saint Gratien; Pierre Tiollais, Paris; Patrick Charnay, Bourg-La-Reine, all of France

[73] Assignees: Institut Pasteur; Institut National de la Sante et de la Recherche Medicale, both of Paris, France

[21] Appl. No.: 640,494

[22] Filed: Jan. 14, 1991

Related U.S. Patent Documents

Reissue of:

[64] Patent No.: 4,428,941
Issued: Jan. 31, 1984
Appl. No.: 261,199
Filed: Aug. 29, 1980

[30] Foreign Application Priority Data

Aug. 30, 1979 [FR] France ..... 79 21811
Apr. 22, 1980 [FR] France ..... 80 09039

[51] Int. Cl.[5] ..... C07K 7/06; C07K 13/00; A61K 37/02

[52] U.S. Cl. ..... 530/329; 530/330; 530/350; 530/403; 530/808; 530/826; 530/324; 435/69.3; 435/172.3; 930/10; 930/223; 935/10; 935/12; 935/31; 935/65

[58] Field of Search ..... 530/324, 350, 329, 330, 530/826; 514/16, 17

[56] References Cited

FOREIGN PATENT DOCUMENTS 13828 6/1980 European Pat. Off. .
7921811 8/1979 France .
8009039 4/1980 France .

OTHER PUBLICATIONS

Galibert et al., Nature, 281, 646–650 (1979).
Pasek et al., Nature, 282, 575–579 (1979).
Valenzuela et al., Nature 280, 815–819 (1979).
Charnay et al., Nature, 286, 893–895 (1980).
Sninsky et al., Nature, 279, 346–348 (1979).
Burrell et al., Nature, 279, 43–47 (1979).

*Primary Examiner*—F. T. Moezie
*Attorney, Agent, or Firm*—Finnegan, Henderson, Farabow, Garrett & Dunner

[57] ABSTRACT

Nucleic acid of reduced size and vector containing said nucleotidic sequence of which DNA codes an immunogenic peptidic sequence capable of inducing the generation of antibodies to the virus of viral hepatitis B. It comprises totally or partly the sequence of nucleotides represented in FIG. 3A. Application to the production by cloning in a bacterium of an immunogenic protein immunizing against hepatitis B, or application to the obtention of probes for the diagnosis of the presence of Dane particles in a serum.

3 Claims, 13 Drawing Sheets

HBV DNA
GENE S

HhaI
HbaI
HhaI
HhaI
1084 p.b.

XbaI
S1+
"EcoRI linkers"

XbaI
pBRHBs
EcoRI

XbaI
EcoRI+XbaI
980p.b
SpCTAGACTCGTGGTGG

S1+
"EcoRI linkers"
p XbaHBs
EcoRI

SpAATTCCCGTGGTGG
(pXbaHBs-1)
SpAATTCCGTGGTGG
(pXbaHBs-2)
SpAATTCCCTCGTGGTGG
(pXbaHBs-3)

EcoRI
fragment HBs $f_2$ →

Fig. 3A.

| | | | | | | | | | | |
|---|---|---|---|---|---|---|---|---|---|---|
| | | | | | | | | | | 30 |
| 3′ | TAC | CTC | TTG | TAG | TGT | AGT | CCT | AAG | GAT | CCT |
| 5′ | ATG | GAG | AAC | ATC | ACA | TCA | GGA | TTC | CTA | GGA |
| | MET | GLU | ASN | ILE | THR | SER | GLY | PHE | LEU | GLY |
| | | | | | | | | | | 60 |
| | GCG | GAA | GAG | CAC | AAT | GTC | CGC | CCC | AAA | AAG |
| | CCC | CTT | CTC | GTG | TTA | CAG | GCG | GGG | TTT | TTC |
| | PRO | LEU | LEU | VAL | LEU | GLN | ALA | GLY | PHE | PHE |
| | | | | | | | | | | 90 |
| | AAC | AAC | TGT | TCT | TAG | GAG | TGT | TAT | GGC | GTC |
| | TTG | TTG | ACA | AGA | ATC | CTC | ACA | ATA | CCG | CAG |
| | LEU | LEU | THR | ARG | ILE | LEU | THR | ILE | PRO | GLN |
| | | | | | | | | | | 120 |
| | TCA | GAT | CTG | AGC | ACC | ACC | TGA | AGA | GAG | TTA |
| | AGT | CTA | GAC | TCG | TGG | TGG | ACT | TCT | CTC | AAT |
| | SER | LEU | ASP | SER | TRP | TRP | THR | SER | LEU | ASN |
| | | | | | | | | | | 150 |
| | AAA | GAT | CCC | CCT | TGA | TGG | CAC | ACA | GAA | CCG |
| | TTT | CTA | GGG | GGA | ACT | ACC | GTG | TGT | CTT | GGC |
| | PHE | LEU | GLY | GLY | THR | THR | VAL | CYS | LEU | GLY |
| | | | | | | | | | | 180 |
| | GTT | TTA | AGC | GTC | AGG | GGT | TGG | AGG | TTA | GTG |
| | CAA | AAT | TCG | CAG | TCC | CCA | ACC | TCC | AAT | CAC |
| | GLN | ASN | SER | GLN | SER | PRO | THR | SER | ASN | HIS |
| | | | | | | | | | | 210 |
| | AGT | GGT | TGG | AGA | ACA | GGA | GGT | TGA | ACA | GGA |
| | TCA | CCA | ACC | TCT | TGT | CCT | CCA | ACT | TGT | CCT |
| | SER | PRO | THR | SER | CYS | PRO | PRO | THR | CYS | PRO |
| | | | | | | | | | | 240 |
| | CCA | ATA | GCG | ACC | TAC | ACA | GAC | GCC | GCA | AAA |
| | GGT | TAT | CGC | TGG | ATG | TGT | CTG | CCG | CGT | TTT |
| | GLY | TYR | ARG | TRP | MET | CYS | LEU | ARG | ARG | PHE |

Fig.3B.

| | | | | | | | | | |
|---|---|---|---|---|---|---|---|---|---|
| | | | | | | | | | 270 |
| TAG | TAG | AAG | GAG | AAG | TAG | GAC | GAC | GAT | ACG |
| ATC | ATC | TTC | CTC | TTC | ATC | CTG | CTG | CTA | TGC |
| ILE | ILE | PHE | LEU | PHE | ILE | LEU | LEU | LEU | CYS |
| | | | | | | | | | 300 |
| GAG | TAG | AAG | AAC | AAC | CAA | GAA | GAC | CTG | ATA |
| CTC | ATC | TTC | TTG | TTG | GTT | CTT | CTG | GAC | TAT |
| LEU | ILE | PHE | LEU | LEU | VAL | LEU | LEU | ASP | TYR |
| | | | | | | | | | 330 |
| GTT | CCA | TAC | AAC | GGG | CAA | ACA | GGA | GAT | TAA |
| CAA | GGT | ATG | TTG | CCC | GTT | TGT | CCT | CTA | ATT |
| GLN | GLY | MET | LEU | PRO | VAL | CYS | PRO | LEU | ILE |
| | Site Bam HI | | | | | | | | 360 |
| GGT | CCT | AGG | AGT | TGT | TGG | TCG | TGC | CCT | GGT |
| CCA | GGA | TCC | TCA | ACA | ACC | AGC | ACG | GGA | CCA |
| PRO | GLY | SER | SER | THR | THR | SER | THR | GLY | PRO |
| | | | | | | | | | 390 |
| ACG | GCC | TGG | ACG | TAC | TGA | TGA | CGA | GTT | CCT |
| TGC | CGG | ACC | TGC | ATG | ACT | ACT | GCT | CAA | GGA |
| CYS | ARG | THR | CYS | MET | THR | THR | ALA | GLN | GLY |
| | | | | | | | | | 420 |
| TGG | AGA | TAC | ATA | GGG | AGG | ACA | ACG | ACA | TGG |
| ACC | TCT | ATG | TAT | CCC | TCC | TGT | TGC | TGT | ACC |
| THR | SER | MET | TYR | PRO | SER | CYS | CYS | CYS | THR |
| | | | | | | | | | 450 |
| TTT | GGA | AGC | CTG | CCT | TTA | ACG | TGG | ACA | TAA |
| AAA | CCT | TCG | GAC | GGA | AAT | TGC | ACC | TGT | ATT |
| LYS | PRO | SER | ASP | GLY | ASN | CYS | THR | CYS | ILE |
| | | | | | | | | | 480 |
| GGG | TAG | GGT | AGT | AGG | ACC | CGA | AAG | CCT | TTT |
| CCC | ATC | CCA | TCA | TCC | TGG | GCT | TTC | GGA | AAA |
| PRO | ILE | PRO | SER | SER | TRP | ALA | PHE | GLY | LYS |

Fig.3C.

510

AAG GAT ACC CTC ACC CGG AGT CGG GCA AAG
TTC CTA TGG GAG TGG GCC TCA GCC CGT TTC

Site HaeIII

PHE LEU TRP GLU TRP ALA SER ALA ARG PHE

540

AGG ACC GAG TCA AAT GAT CAC GGT AAA CAA
TCC TGG CTC AGT TTA CTA GTG CCA TTT GTT
SER TRP LEU SER LEU LEU VAL PRO PHE VAL

570

GTC ACC AAG CAT CCC GAA AGG GGG TGA CAA
CAG TGG TTC GTA GGG CTT TCC CCC ACT GTT
GLN TRP PHE VAL GLY LEU SER PRO THR VAL

600

ACC GAA AGT CAA TAT ACC TAC TAC ACC ATA
TGG CTT TCA GTT ATA TGG ATG ATG TGG TAT
TRP LEU SER VAL ILE TRP MET MET TRP TYR

630

ACC CCC GGT TCA GAC ATG TCG TAG AAC TCA
TGG GGG CCA AGT CTG TAC AGC ATC TTG AGT
TRP GLY PRO SER LEU TYR SER ILE LEU SER

690

GGG AAA AAT GGC GAC AAT GGT TAA AAG AAA
CCC TTT TTA CCG CTG TTA CCA ATT TTC TTT
PRO PHE LEU PRO LEU LEU PRO ILE PHE PHE

ACA GAA ACC CAT ATG TAA ATT 5'
TGT CTT TGG GTA TAC ATT TAA 3'
CYS LEU TRP VAL TYR ILE STOP

Fig.4A.

| | | | | | |
|---|---|---|---|---|---|
| | | | 2191 2200 | 2210 | 2220 |
| | | | 5′ TTGACATAC | TTTCCAATCA | ATAGGCCTGT |
| | | | 3′ AACTGTATG | AAAGGTTAGT | TATCCGGACA |
| 2230 | 2240 | 2250 | 2260 | 2270 | 2280 |
| TAATAGGAAG | TTTTCTAAAA | CATTCTTTGA | TTTTTTGTAT | GATGTGTTCT | TGTGGCAAGG |
| ATTATCCTTC | AAAAGATTTT | GTAAGAAACT | AAAAAACATA | CTACACAAGA | ACACCGTTCC |
| 2290 | 2300 | 2310 | 2320 | 2330 | 2340 |
| ACCCATAACA | TCCAATGACA | TAACCCATAA | AATTTAGAGA | GTAACCCCAT | CTCTTTGTTT |
| TGGGTATTGT | AGGTTACTGT | ATTGGGTATT | TTAAATCTCT | CATTGGGGTA | GAGAAACAAA |
| 2350 | 2360 | 2370 | 2380 | 2390 | 2400 |
| TGTTAGGGTT | TAAATGTATA | CCCAAAGACA | AAAGAAAATT | GGTAACAGCG | GTAAAAAGGG |
| ACAATCCCAA | ATTTACATAT | GGGTTTCTGT | TTTCTTTTAA | CCATTGTCGC | CATTTTTCCC |
| 2410 | 2420 | 2430 | 2440 | 2450 | 2460 |
| ACTCAAGATG | CTGTACAGAC | TTGGCCCCCA | ATACCACATC | ATCCATATAA | CTGAAAGCCA |
| TGAGTTCTAC | GACATGTCTG | AACCGGGGGT | TATGGTGTAG | TAGGTATATT | GACTTTCGGT |
| 2470 | 2480 | 2490 | 2500 | 2510 | 2520 |
| AACAGTGGGG | GAAAGCCCTA | CGAACCACTG | AACAAATGGC | ACTAGTAAAC | TGAGCCAGGA |
| TTGTCACCCC | CTTTCGGGAT | GCTTGGTGAC | TTGTTTACCG | TGATCATTTG | ACTCGGTCCT |
| 2530 | 2540 | 2550 | 2560 | 2570 | 2580 |
| GAAACGGGCT | GAGGCCCACT | CCCATAGGAA | TTTTCCGAAA | GCCCAGGATG | ATGGGATGGG |
| CTTTGCCCGA | CTCCGGGTGA | GGGTATCCTT | AAAAGGCTTT | CGGGTCCTAC | TACCCTACCC |
| 2590 | 2600 | 2610 | 2620 | 2630 | 2640 |
| AATACAGGTG | CAATTTCCGT | CCGAAGGTTT | GGTACAGCAA | CAGGAGGGAT | ACATAGAGGT |
| TTATGTCCAC | GTTAAAGGCA | GGCTTCCAAA | CCATGTCGTT | GTCCTCCCTA | TGTATCTCCA |
| 2650 | 2660 | 2670 | 2680 | 2690 | 2700 |
| TCCTTGAGCA | GTAGTCATGC | AGGTCCGGCA | TGGTCCCGTG | CTGGTTGTTG | AGGATCCTGG |
| AGGAACTCGT | CATCAGTACG | TCCAGGCCGT | ACCAGGGCAC | GACCAACAAC | TCCTAGGACC |
| 2710 | 2720 | 2730 | 2740 | 2750 | 2760 |
| AATTAGAGGA | CAAACGGGCA | ACATACCTTG | ATAGTCCAGA | AGAACCAACA | AGAAGATGAG |
| TTAATCTCCT | GTTTGCCCGT | TGTATGGAAC | TATCAGGTCT | TCTTGGTTGT | TCTTCTACTC |
| 2770 | 2780 | 2790 | 2800 | 2810 | 2820 |
| GCATAGCAGC | AGGATGAAGA | GGAAGATGAT | AAAACGCCGC | AGACACATCC | AGCGATAACC |
| CGTATCGTCG | TCCTACTTCT | CCTTCTACTA | TTTTGCGGCG | TCTGTGTAGG | TCGCTATTGG |

Fig.4B.

| 2830 | 2840 | 2850 | 2860 | 2870 | 2880 |
|---|---|---|---|---|---|
| AGGACAAGTT | GGAGGACAAG | AGGTTGGTGA | GTGATTGGAG | GTTGGGGACT | GCGAATTTTG |
| TCCTGTTCAA | CCTCCTGTTC | TCCAACCACT | CACTAACCTC | CAACCCCTGA | CGCTTAAAAC |
| 2890 | 2900 | 2910 | 2920 | 2930 | 2940 |
| GCCAAGACAC | ACGGTAGTTC | CCCCTAGAAA | ATTGAGAGAA | GTCCACCACG | AGTCTAGACT |
| CGGTTCTGTG | TGCCATCAAG | GGGGATCTTT | TAACTCTCTT | CAGGTGGTGC | TCAGATCTGA |
| 2950 | 2960 | | | | |
| CTGCGGTATT | GTGAGGATTC | TTG L 3′ | | | |
| GACGCCATAA | CACTCCTAAG | AAC S 5′ | | | |

$f_2$ ←

Fig.5.

| | | | | | | | | | | | | | | |
|---|---|---|---|---|---|---|---|---|---|---|---|---|---|---|
| | | | 24 | | | | | | 30 | | | | | |
| | | | ARG | ILE | LEU | THR | ILE | PRO | GLN | SER | LEU | ASP | SER | TRP |
| | | | | 40 | | | | | | | | | | 50 |
| TRP | THR | SER | LEU | ASN | PHE | LEU | GLY | GLY | THR | THR | VAL | CYS | LEU | GLY |
| | | | | | | | | | 60 | | | | | |
| GLN | ASN | SER | GLN | SER | PRO | THR | SER | ASN | HIS | SER | PRO | THR | SER | CYS |
| | | | | 70 | | | | | | | | | | 80 |
| PRO | PRO | THR | CYS | PRO | GLY | TYR | ARG | TRP | MET | CYS | LEU | ARG | ARG | PHE |
| | | | | | | | | | 90 | | | | | |
| ILE | ILE | PHE | LEU | PHE | ILE | LEU | LEU | LEU | CYS | LEU | ILE | PHE | LEU | LEU |
| | | | | 100 | | | | | | | | | | 110 |
| VAL | LEU | LEU | ASP | TYR | GLN | GLY | MET | LEU | PRO | VAL | CYS | PRO | LEU | ILE |
| | | | | | | | | | 120 | | | | | |
| PRO | GLY | SER | SER | THR | THR | SER | THR | GLY | PRO | CYS | ARG | THR | CYS | MET |
| | | | | 130 | | | | | | | | | | 140 |
| THR | THR | ALA | GLN | GLY | THR | SER | MET | TYR | PRO | SER | CYS | CYS | CYS | THR |
| | | | | | | | | | 150 | | | | | |
| LYS | PRO | SER | ASP | GLY | ASN | CYS | THR | CYS | ILE | PRO | ILE | PRO | SER | SER |
| | | | | 160 | | | | | | | | | | 170 |
| TRP | ALA | PHE | GLY | LYS | PHE | LEU | TRP | GLU | TRP | ALA | SER | ALA | ARG | PHE |
| | | | | | | | | | 180 | | | | | |
| SER | TRP | LEU | SER | LEU | LEU | VAL | PRO | PHE | VAL | GLN | TRP | PHE | VAL | GLY |
| | | | | 190 | | | | | | | | | | 200 |
| LEU | SER | PRO | THR | VAL | TRP | LEU | SER | VAL | ILE | TRP | MET | MET | TRP | TYR |
| | | | | | | | | | 210 | | | | | |
| TRP | GLY | PRO | SER | LEU | TYR | SER | ILE | LEU | SER | PRO | PHE | LEU | PRO | LEU |
| | | | | 220 | | | | | | 226 | | | | |
| LEU | PRO | ILE | PHE | PHE | CYS | LEU | TRP | VAL | TYR | ILE | | | | |

Fig.6.

$f_2$ →

| | | | | | | | | | | | | | | | | | | | |
|---|---|---|---|---|---|---|---|---|---|---|---|---|---|---|---|---|---|---|---|
| | | | | | | | | | | | | | | | | | | | 360 |
| | | | | | | | | | | | | AGG | AGT | TGT | TGG | TCG | TGC | CCT | GGT |
| | | | | | | | | | | | | TCC | TCA | ACA | ACC | AGC | ACG | GGA | CCA |
| | | | | | | | | | | | | SER | SER | THR | THR | SER | THR | GLY | PRO |
| | | | | | | | | | 390 | | | | | | | | | | 420 |
| ACG | GCC | TGG | ACG | TAC | TGA | TGA | CGA | GTT | CCT | TGG | AGA | TAC | ATA | GGG | AGG | ACA | ACG | ACA | TGG |
| TGC | CGG | ACC | TGC | ATG | ACT | ACT | GCT | CAA | GGA | ACC | TCT | ATG | TAT | CCC | TCC | TGT | TGC | TGT | ACC |
| CYS | ARG | THR | CYS | MET | THR | THR | ALA | GLN | GLY | THR | SER | MET | TYR | PRO | SER | CYS | CYS | CYS | THR |
| | | | | | | | | | | | | | | | | | | | 480 |
| TTT | GGA | AGC | CTG | CCT | TTA | ACG | TGG | ACA | TAA | GGG | TAG | GGT | AGT | AGG | ACC | CGA | AAG | CCT | TTT |
| AAA | CCT | TCG | GAC | GGA | AAT | TGC | ACC | TGT | ATT | CCC | ATC | CCA | TCA | TCC | TGG | GCT | TTC | GGA | AAA |
| LYS | PRO | SER | ASP | GLY | ASN | CYS | THR | CYS | ILE | PRO | ILE | PRO | SER | SER | TRP | ALA | PHE | GLY | LYS |
| AAG | GAT | ACC | CTC | ACC | | | | | | | | | | | | | | | |
| TTC | CTA | TGG | GAG | TGG | | | | | | | | | | | | | | | |
| PHE | LEU | TRP | GLU | TRP | | | | | | | | | | | | | | | |

Fig. 7A.

Ava III (2116) HhaI (1952) HincII (2191)

| | | | | | |
|---|---|---|---|---|---|
| 1930 | 1940 | 1950 | 1960 | 1970 | 1980 |
| TCGGCAGAGG | AGCCGAAAAG | GTTCCACGCA | TGCGCTGATG | GCCCATGACC | AAGCCCCAGC |
| AGCCGTCTCC | TCGGCTTTTC | CAAGGTGCGT | ACGCGACTAC | CGGGTACTGG | TTCGGGGTCG |
| 1990 | 2000 | 2010 | 2020 | 2030 | 2040 |
| CAGTGGGGGT | TGCGTCAGCA | AACACTTGGC | ACAGACCTGG | CCGTTGCCGG | GCAACGGGGT |
| GTCACCCCCA | ACGCAGTCGT | TTGTGAACCG | TGTCTGGACC | GGCAACGGCC | CGTTGCCCCA |
| 2050 | 2060 | 2070 | 2080 | 2090 | 2100 |
| AAAGGTTCAG | GTATTGTTTA | CACAGAAAGG | CCTTGTAAGT | TGGCGAGAAA | GTGAAAGCCT |
| TTTCCAAGTC | CATAACAAAT | GTGTCTTTCC | GGAACATTCA | ACCGCTCTTT | CACTTTCGGA |
| 2110 | 2120 | 2130 | 2140 | 2150 | 2160 |
| GCTTAGATTG | AATACATGCA | TACAAAGGCA | TCAACGCAGG | ATAACCACAT | TGTGTAAAAG |
| CGAATCTAAC | TTATGTACGT | ATGTTTCCGT | AGTTGCGTCC | TATTGGTGTA | ACACATTTTC |
| 2170 | 2180 | 2190 | 2200 | 2210 | 2220 |
| GGGCAGCAAA | ACCCAAAAGA | CCCACAATTC | GTTGACATAC | TTTCCAATCA | ATAGGCCTGT |
| CCCGTCGTTT | TGGGTTTTCT | GGGTGTTAAG | CAACTGTATG | AAAGGTTAGT | TATCCGGACA |
| 2230 | 2240 | 2250 | 2260 | 2270 | 2280 |
| TAATAGGAAG | TTTTCTAAAA | CATTCTTTGA | TTTTTTGTAT | GATGTGTTCT | TGTGGCAAGG |
| ATTATCCTTC | AAAAGATTTT | GTAAGAAACT | AAAAAACATA | CTACACAAGA | ACACCGTTCC |
| 2290 | 2300 | 2310 | 2320 | 2330 | 2340 |
| ACCCATAACA | TCCAATGACA | TAACCCATAA | AATTTAGAGA | GTAACCCCAT | CTCTTTGTTT |
| TGGGTATTGT | AGGTTACTGT | ATTGGGTATT | TTAAATCTCT | CATTGGGGTA | GAGAAACAAA |
| 2350 | 2360 | 2370 | 2380 | 2390 | 2400 |
| TGTTAGGGTT | TAAATGTATA | CCCAAAGACA | AAAGAAAATT | GGTAACAGCG | GTAAAAAGGG |
| ACAATCCCAA | ATTTACATAT | GGGTTTCTGT | TTTCTTTTAA | CCATTGTCGC | CATTTTTCCC |
| 2410 | 2420 | 2430 | 2440 | 2450 | 2460 |
| ACTCAAGATG | CTGTACAGAC | TTGGCCCCCA | ATACCACATC | ATCCATATAA | CTGAAAGCCA |
| TGAGTTCTAC | GACATGTCTG | AACCGGGGGT | TATGGTGTAG | TAGGTATATT | GACTTTCGGT |
| 2470 | 2480 | 2490 | 2500 | 2510 | 2520 |
| AACAGTGGGG | GAAAGCCCTA | CGAACCACTG | AACAAATGGC | ACTAGTAAAC | TGAGCCAGGA |
| TTGTCACCCC | CTTTCGGGAT | CGTTGGTGAC | TTGTTTACCG | TGATCATTTG | ACTCGGTCCT |

t S

Fig. 7B.

| | | | | | |
|---|---|---|---|---|---|
| 2530 | 2540 | 2550 | 2560 | 2570 | 2580 |
| GAAACGGGCT | GAGGCCCACT | CCCATAGGAA | TTTTCCGAAA | GCCCAGGATG | ATGGGATGGG |
| CTTTGCCCGA | CTCCGGGTGA | GGGTATCCTT | AAAAGGCTTT | CGGGTCCTAC | TACCCTACCC |
| 2590 | 2600 | 2610 | 2620 | 2630 | 2640 |
| AATACAGGTG | CAATTTCCGT | CCGAAGGTTT | GGTACAGCAA | CAGGAGGGAT | ACATAGAGGT |
| TTATGTCCAC | GTTAAAGGCA | GGCTTCCAAA | CCATGTCGTT | GTCCTCCCTA | TGTATCTCCA |
| 2650 | 2660 | 2670 | 2680 | 2690 | 2700 |
| TCCTTGAGCA | GTAGTCATGC | AGGTCCGGCA | TGGTCCCGTG | CTGGTTGTTG | AGGATCCTGG |
| AGGAACTCGT | CATCAGTACG | TCCAGGCCGT | ACCAGGGCAC | GACCAACAAC | TCCTAGGACC |
| 2710 | 2720 | 2730 | 2740 | 2750 | 2760 |
| AATTAGAGGA | CAAACGGGCA | ACATACCTTG | ATAGTCCAGA | AGAACCAACA | AGAAGATGAG |
| TTAATCTCCT | GTTTGCCCGT | TGTATGGAAC | TATCAGGTCT | TCTTGGTTGT | TCTTCTACTC |
| 2770 | 2780 | 2790 | 2800 | 2810 | 2820 |
| GCATAGCAGC | AGGATGAAGA | GGAAGATGAT | AAAACGCCGC | AGACACATCC | AGCGATAACC |
| CGTATCGTCG | TCCTACTTCT | CCTTCTACTA | TTTTGCGGCG | TCTGTGTAGG | TCGCTATTGG |
| 2830 | 2840 | 2850 | 2860 | 2870 | 2880 |
| AGGACAAGTT | GGAGGACAAG | AGGTTGGTGA | GTGATTGGAG | GTTGGGGACT | GCGAATTTTG |
| TCCTGTTCAA | CCTCCTGTTC | TCCAACCACT | CACTAACCTC | CAACCCCTGA | CGCTTAAAAC |
| 2890 | 2900 | 2910 | 2920 | 2930 | 2940 |
| GCCAAGACAC | ACGGTAGTTC | CCCCTAGAAA | ATTGAGAGAA | GTCCACCACG | AGTCTAGACT |
| CGGTTCTGTG | TGCCATCAAG | GGGGATCTTT | TAACTCTCTT | CAGGTGGTGC | TCAGATCTGA |
| 2950 | 2960 | 2970 | 2980 | 2990 | 3000 |
| CTGCGGTATT | GTGAGGATTC | TTGTCAACAA | GAAAAACCCC | GCCTGTAACA | CGAGAAGGGG |
| GACGCCATAA | CACTCCTAAG | AACAGTTGTT | CTTTTTGGGG | CGGACATTGT | GCTCTTCCCC |
| 3010 | 3020 | 3030 | 3040 | 3050 | 3060 |
| TCCTAGGAAT | CCTGATGTGA | TGTTCTCCAT | GTTCAGCGCA | GGGTCCCCAA | TCCTCGAGAA |
| AGGATCCTTA | GGACTACACT | ACAAGAGGTA | CAAGTCGCGT | CCCAGGGGTT | AGGAGCTCTT |
| 3070 | 3080 | 3090 | 3100 | 3110 | 3120 |
| GATTGACGAT | AAGGGAGAGG | CAGTAGTCAG | AACAGGGTTT | ACTGTTCCTG | AACTGGAGCC |
| CTAACTGCTA | TTCCCTCTCC | GTCATCAGTC | TTGTCCCAAA | TGACAAGGAC | TTGACCTCGG |

HincII(2963) HhaI(3036)

p"S" AvaI(3053)

Fig.7C.

| 3130 | 3140 | 3150 | 3160 | 3170 | 3180 |
|---|---|---|---|---|---|
| ACCAGCAGGG | AAATACAGGC | CTCTCACTCT | GGGATCTTGC | AGAGTTTGGT | GGAAGGTTGT |
| TGGTCGTCCC | TTTATGTCCG | GAGAGTGAGA | CCCTAGAACG | TCTCAAACCA | CCTTCCAACA |

GG L 3′
CC S 5′

$f_2$

EcoRI (1/3182)

NUCLEOTIDIC SEQUENCE CODING THE SURFACE ANTIGEN OF THE HEPATITIS B VIRUS, VECTOR CONTAINING SAID NUCLEOTIDIC SEQUENCE, PROCESS ALLOWING THE OBTENTION THEREOF AND ANTIGEN OBTAINED THEREBY

Matter enclosed in heavy brackets [ ] appears in the original patent but forms no part of this reissue specification; matter printed in italics indicates the additions made by reissue.

The invention relates to a nucleic acid comprising a nucleotide sequence capable of coding an immunogenic peptide sequence corresponding to the surface antigen of the virus of viral hepatitis B, and to the polypeptides and peptides obtained.

It relates also to a process enabling such a nucleic acid to be obtained.

Hepatitis B is a frequent viral disease particularly in Tropical Africa, in South East Asia and in the Far East.

The etiological agent is a virus (HBV) or Dane particle, comprising an envelope (Australia antigen or HBs antigen), a capsid (HBc antigen), and endogenic polymerase and a partly single strand circular DNA molecule; the longest strand of this DNA molecule includes close to 3,200 nucleotides (SUMMERS J., O'CONNELL / A. et MILLMAN I. (1975) Proc. Nat. Acad. Sci. USA 72, 4 597–4 601).

The endogenic DNA polymerase can be used to repair the shorter strand in vitro (T. A. LANDERS, H. B. GREENBERT and J. S. ROBINSON, J. VIROL., 23, 1977, p. 368–376).

Electrophoretic analysis of the proteins of the envelope has shown the presence of 2 to 7 polypeptides of which the principal are called: polypeptide I and polypeptide II (PETERSON D. L., ROBERTS I. M. and VYAS G. N. (1977) Proc. Nat. Acad. Sci. USA, 74, 1,530–1,534, and PETERSON D. L., CHIEN D. Y., VYAS G. N., NITECHKI D. and BOND H. (1978) in viral Hepatitis, ed. G. VYAS, S. COHEN and R. SCHMID, The Franklin Institute Press, Philadelphia, 569–573).

The Polypeptide I has a weight of 22,000 to 26,000 daltons. Polypeptide II is glycosylated and has a molecular weight of 28,000 to 30,000 daltons. The amino acid composition of these two polypeptides is very similar, the sequences which form, respectively, their 15 first amino-acids (from the N-terminal end) and their last 3 amino-acids are identical, so that the hypothesis has formulated that polypeptide II could differ from polypeptide I only by a glycosylation.

Study of the virus is extremely difficult to the extent that no cell culture system is available enabling the propagation of the virus. This difficulty has already in part been overcome, more particularly as regards the ayw serotype. The who DNA (genome) of the virus has been identified and cloned, notably in E. coli, after its previous insertion in the single EcoRI site of a λgt. WES. λB vector, according to the technique by FRITSCH A., POURCEL C., CHARNAY P. and TIOLLAIS P. (1978) C. R. Acad. de Paris, 287, 1,453–1,456).

Until now, the sequence of the I and II polypeptides themselves, and the location in the viral DNA of the sequence coding these peptides have not been done.

It is an object of the invention to provide a much smaller DNA sequence than the viral DNA itself, containing the sequence adapted to code the peptide sequence endowed with immunogenic properties enabling, when it is introduced into the organism of a living host, to induct the formation by the latter of antibodies capable of protecting this same host subsequently with respect to the virus of viral hepatitus B, notably when the latter is in virulent state.

The invention stems not only from the complete nucleotide analysis of the genome of the Dane particle which the inventors have achieved, but to the idea that they have had for identifying the coding gene (called below "S gene") of the abovesaid polypeptides, to search in the complete nucleotide structure thus preestablished of the genome of the Dane particle, for those of the sequences of the nucleotides capable of coding the known proximal and terminal peptide sequences of these polypeptides.

It will be recalled the PETERSON and co-workers have reported, notably in the articles of which the references are recalled above, that the proximal sequence (first N-terminal amino-acid) of the 15 first amino-acids is in principle as follows: met glu asn ile thr ser gly phe leu gly pro leu leu val ser and that the terminal sequence of these same polypeptides (last C-terminal amino-acid) was the following:

val tyr ile

FIG. 2 is a diagramatic chart of a vector;

FIG. 3a, 3b and 3c show the nucleotide structure of the gene S and the polypeptide chain resulting from the translation of the gene;

FIG. 4a and 4b show the two mutually complementary strands of DNA sequence;

FIG. 5 shows the peptidic sequence coded by nucleotide sequence, and

FIG. 6 shows a nucleotide containing a peptide sequence according to the invention.

*FIGS. 7A–7C illustrate the terminal portion of the genome of the S gene, between positions 60.4 and 100 (in % length of DNA).*

FIG. 1 is a diagrammatic chart of the genome of the Dane particle. The latter includes two strands $b_1$ and $b_2$; the shortest of them ($b_2$) being normally devoid of the portion represented by an interrupted line in the drawing.

It is known that this DNA only includes a single EcoRI site.

The arrow $f_1$ gives the direction of numbering of the nucleotides from which the longest strand $b_1$ is composed, and the arrow $f_2$ gives the direction of the transcription of the DNA of the virus, notably by the cellular mechanism of the cells invaded by the virus of hepatitis B, as regards the expression of the gene S.

The EcoRI site can hence be numbered 0 or, as has now been determined more exactly for that of the hepatitis B virus belonging to the serotype ayw, 3,182.

The inner circle e in continuous line gives the scale in % of the length of the DNA and permits the positions of certain of its parts to be specified.

The numbers 3', 5' and 5', 3' at the lower part of the chart are aimed at the terminal ends bearing the same numbers in conventional representation of the ends of the nucleic acid chains.

Figure 1:
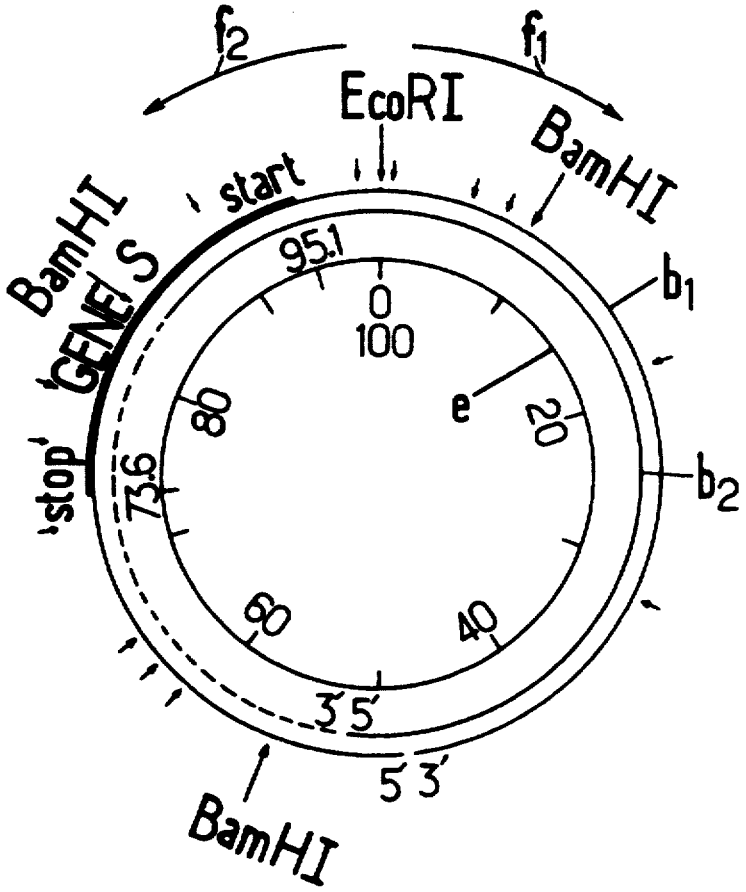
FIG. 1 is a diagramatic chart of the genome of the Dane particle.

According to the invention it has been shown that the "gene S" constituted essentially the fragment of the longest strand $b_1$ situated between the positions 73.6 and 95.1 of the diagrammatic map of FIG. 1. The abbreviation "Start" and "Stop" represent the intiation and stopping points of the transcription of the "gene S".

FIGS. [2A, 2B, 2C] *7A, 7B, 7C,* are representative of the terminal portion of the abovesaid genome, comprised notably between the positions 60.4 and 100 (in % length of DNA). Each of the letters shown in FIG. 2 correspond conventionally to one of the 4 basic nucleotides of DNA:

A: Adenine
G: Guanine
T: Thymine
C: Cytosine

The lower lines, in each pair of lines from which FIGS. [2A, 2B, 2C] *7A, 7B, 7C* are constituted, correspond to the nucleic acid corresponding to the nucleotide chain $b_2$.

The analytical technique used to establish the more detailed map represented by FIGS. [2A, 2B, 2C] *7A, 7B, 7C,* will be briefly recalled below.

The characterisation of the nucletide of the "gene S" such as proposed within the scope of the present invention, and of which the proximal ends p "S" and terminal ends t, "S" are indicated in FIGS. [2A, 2B, 2C] *7A, 7B, 7C,* results from the observation that:

the first 14 triplets (in the direction of reading $f_2$) from the nucleotide numbered 3 030 with respect to the EcoRI terminal end, are respectively capable of coding the 14 first amino-acids of the proximal sequence of the 15 first amino-acids of the abovesaid polypeptides, the 4 last triplets GTA TAC ATT TAA read in the complementary chain $b_2$ to the transcribed chain $b_1$ correspond respectively to the 3 terminal amino-acids of the abovesaid polypeptides and to a stop codon;

this sequence of nucleotides (678 nucleotides) does not comprise any stop codon, at least when the reading frame is adopted implying that the first triplet "read" on the DNA by the cellular mechanism is AUG, (corresponding to a strand complementary to ATG);

the complete translation of the genetic information commencing with the initial codon ATG leads to a theoretical polypeptide of 226 amino-acids, having a molecular weight of 25, 422 daltons.

The nucleotide structure of the "gene S" as well as the polypeptide chain resulting form the translation of the "gene S" are shown in FIGS. 3A, 3B, 3C.

These values are quite in accordance with the analytical data which result from the electrophoretic mobility of the polypeptide I on polyacrylamide gels which have already been described by the preceding authors (references 9–12 according to the bibliography figuring at the end of the description of the present patent application).

The difference observed at the level of the 15th amino-acid of the proximal peptide sequence of the polypeptide I: leucine according to the charts of FIGS. [2A, 2B, 2C] *7A, 7B, 7C,* and 3A, 3B, 3C mentioned above, and not serine according to the observation of the abovesaid authors, may perhaps be attributed to the fact that these authors have worked with a genetic variant different from that which is the subject of the present study. It will be noted that the difference can besides be attributed to the substitution of a single nucleotide in the "TTA" triplet concerned in the particular "gene S" shown in the maps of FIGS. [2A, 2B, 2C] *7A, 7B, 7C* and 3A, 3B, 3C, instead of "TCA", one of the triplets capable of being translated into serine.

The invention hence relates more particularly to the fragments of the nucleic acid which can be excised from the DNA of the Dane particle, these fragments being more particularly characterised in that they contain the portion of the "gene S" capable of coding the portion of the protein of the envelope of the virus which is responsible for the immunological properties of the hepatitis B virus.

Accordingly, the invention relates therefore to a nucleic acid comprising at the most of the order of 1,000–1,100 nucleotides, more particularly characterised in that it is adapted to code an immunogenic peptide sequence, itself adapted to induce in vivo the production of active antibodies with respect to the hepatitis B virus, this peptide sequence containing essentially the structure shown in FIGS. 3A, 3B, 3C, or any peptide sequence having equivalent immunogenic properties.

The invention also relates to a vector for the expression of said nucleotide sequence into a micro-organism or into eucaryotic cells on condition that the genetic fusion has been carried out by preserving the reading phase of the "gene S".

The nucleotide sequences used according to the invention have with respect to one another a variability leading, on their expression, to the formation of determinants varying according to the sub-type of the hepatitis B virus (sub-types d, w, y, r of group a).

For one of the peptide sequences shown in FIGS. 3A, 3B, 3C, it will be observed that the first amino-acid of the abovesaid sequence: methionine, is N-terminal and that the amino-acid of the opposite end: isoleucine, is C-terminal.

The invention also relates, more particularly, to the nucleotide sequence represented in FIGS. 4A, 4B, coding the peptide sequence such as results form FIG. 5 or any similar peptide sequence endowed with equivalent immunogen properties.

It is self-evident that by "equivalent peptide sequence", mentioned above, must be understood any peptide sequence in which certain parts may not be strictly identical with corresponding parts of the peptide sequence shown in FIGS. 3A, 3B, 3C and 5, these variations being attributable to local mutations not affecting the general immunogen character of the protein or with structural modifications owing to the different serotypes in which proteins of the type concerned can occur (notably serotypes adw, adr and ayr).

The invention relates more particularly to the nucleotide sequence containing the peptide sequence as shown in FIG. 6 or any similar peptide sequence endowed with equivalent immunogen properties.

The invention relates more particularly again to the following peptide sequences:

Alanine-Glutamine-Glycine-Threonine-Serine
Threonine-Alanine-Glutamine-Glycine-Threonine-Serine
Threonine-Threonine-Alanine-Glutamine-Glycine-Threonine-Serine In the first above-indicated peptide the alanine end is N-terminal and the serine end is C-terminal.

In the second or third abovementioned peptides, the threonine end is N-terminal and the serine end is C-terminal.

By way of example, it is possible notably to prepare the pentapeptide starting from the C-terminal serine to which threonine is fastened by the Castro method described in Tetrahedron Letters, 1975, No. 14, page 1,219–1,222. Then the amino-acids glycine, glutamine, alanine are added by the so-called repeated mixed anhydride method (rema method) described by Beierman in Chemistry and Biology of Peptides, Ed. J. Meienhofer, Ann. Arbour Science Publ., Ann. Arb. Mich. 341 (1972).

The invention also relates to the products resulting from the fixing of the pentapeptide on a larger carrier molecule, notably of the polypeptide or protein type, the composition containing this pentapeptide in fixing products, notably in association with a pharmaceutically acceptable vehicle, and more particularly vaccines against hepatitis B. These pharmaceutical vehicles are suited, conventionally, to the selected method of administration, notably orally, parenterally, rectally or by nebulisation on to the mucous membranes, notably the nasal membranes.

The hexapeptide and the polypeptide with 7 amino-acids can be synthesized by conventional peptide synthesis techniques.

These peptides are, according to the present invention, believed to be the antigen site of the polypeptides of larger size considered above and responsible for the vaccinating power of the viral envelope (Journal of Biol. Stand. 1976, 4, 295–304 RAO et VYAS "Biochemical Characterization of Hepatitis B Surface Antigen in Relation to Serologic Activity").

Again the invention relates also to the DNA fragments capable of coding the production of such pentapeptide, hexapeptide and polypeptide with 7 amino acids. It relates to:

for the pentapeptide, notably the polynucleotide of the formula:

5′ CCT CAA GGA ACC TCT 3′

3′ GGA GTT CCT TGG AGA 5′ for the hexapeptide, notably of the polynucleotide of the formula:

5′ ACT GCT CAA GGA ACC TCT 3′

3′ TGA CGA GTT CCT TGG AGA 5′ for the polypeptide with 7 amino acids the polynucleotide of the formula:

5′ ACT ACT GCT CAA GGA ACC TCT 3′

3′ TGA TGA CGA GTT CCT TGG AGA 5′ or in each of the three cases, of the complementary polynucleotide relating to the three preceding respective polynucleotides or again any polynucleotide in which each of the triplets can be replaced by any similar triplet capable of coding the production of the same amino-acid.

The nucleic acid according to the invention can also be characterised in that it comprises at least one of the two mutually complementary strands of a DNA sequence such as shown in FIGS. 4A, 4B (in which are shown also the numbers corresponding to the positions of the first nucleotides of each of the successive fragments of 10 nucleotides shown with respect to the EcoRI position not shown in the Figure: it is self-evident that these numbers do not come into consideration at the level of characterisation of the nucleotide sequence of the type concerned). This DNA fragment is bounded by two sites.

It will be appreciated that this nucleotide sequence corresponds to the genetic information whose translation leads to the peptide sequence shown in FIG. 5.

The invention relates naturally to equivalent nucleotide sequences with a single strand or double strand, of which notably the strand having the structure which arises from the succession of lower lines of FIGS. 4A, 4B, the corresponding double strand DNA, or the corresponding messenger RNA's, notably that shown by the complementary chains of nucleotides constituted by the lower lines of the pairs of lines of FIGS. 4A, 4B (direction of the arrow $f_2$).

In the same way there come within the field of the invention the nucleotide chains which are differentiated from the preceding ones by certain triplets or small sequences of triplets, to the extent that these nucelotide sequences remain adapted to code a polypeptide preserving the characteristic immunogen activities of the virus of viral hepatitis B. In general, it relates to nucleotide chains which, possibly, after denaturation of the double strand DNA to produce the corresponding single strand nucleic acids, remain capable of hybridizing over at least about 90% of their length with one of the DNA strands of FIGS. 4A, 4B.

Preferred nucleic acids according to the invention are also those which can be excised from DNA of viral hepatitis and which, when they are double strand, are characterised by the existence at one of their ends of an HincII, HhaI, AvaI or EcoRI extremity and at their other end by an AvaIII, HincII or HhaI extremity.

The positions of these various extremities with respect to the EcoRI site are shown diagrammatically in FIGS. [2A, 2B, 2C] *7A, 7B, 7C.*

The nucleic acid according to the invention is intended for incorporation in a vector enabling its expression into a bacteria and into eucaryotic cells, notably for the production of a protein or of a peptide capable of inducing in the organism of a living host the production of active antibodies against the virus of viral hepatitis B. The protein or peptide resulting from the translation of the nucleotide sequence according to the invention can be used as a vaccinating agent or as an agent serving for diagnosis.

The nucleic acid according to the invention can also be used as a probe to track down the presence or not in blood samples or test serum, of the Dane particle, of the HBs antigen or of fragments of the latter, etc. (by the conventional DNA-DNA hybridization technique).

Other characteristics of the invention will result also from the brief description which follows of the techniques of analysis of identification and of production of DNA fragments according to the invention. Reference will naturally be made to the drawings whose Figures have already been taken into consideration in the foregoing. The FIgures or numbers between parentheses correspond to the references of the bibliography appended to the present description.

The invention relates also to particular vectors enabling the expression of the above-described nucleotide sequences, notably in the form of a hybrid protein in which a protein fragment having the immunological character of HBsAg added to a carrier molecule conferring on the whole immunogen or immunoreactive properties, capable of inducing the production of protective antibodies with respect to viral infection in the organism of the host into which this protein has previously been introduced.

In particular, the invention relates to a vector—phage or plasmid—containing at least a part of the lactose operon, more particularly the promoter and the Z gene of this operon, this vector being characterised in that it is modified for the insertion, in phase, in a suitable site of the Z gene, such as the EcoRI site of any one of the DNA fragments of the principal patent, notably those containing the largest part of the "S gene". It relates also to those of these modified vectors, in which a part at least of the coding DNA fragment for the largest part of the β-galactosidase would be replaced by a DNA fragment adapted to code for any other non-immunogenic carrier molecule, or of which the possible immunological properties, if the latter exist, do not interfere with those of the peptide part having the immunological properties of HBsAg, for example essentially that which extends in the direction of readying from its HhaI site.

The invention relates also more particularly to a hybrid protein characterised in that it contains polypeptide sequence having the specific immunological properties of HBsAG, contiguous with a polypeptide sequence constituted for the most part of β-galactosidase, which plays the role of carrier-protein.

The invention does not extend only to this particular hybrid molecule, whose essential role is to constitute a model of a protein constructed according to the techniques of genetic engineering and endowed with immunogen and immunoreactive properties characteristic of the HBsAG antigen, but also to any other hybrid protein in which all or part of the β-galactosidase may be replaced by any other nonimmunogen carrier molecule, or of which the possible immunological properties, if the latter exist, do not interfere with those of the peptide part having the immunological properties of HBsAg.

Figures 1A, 1B, 1C, 1D, 1E, 1F, 1G, 1H:
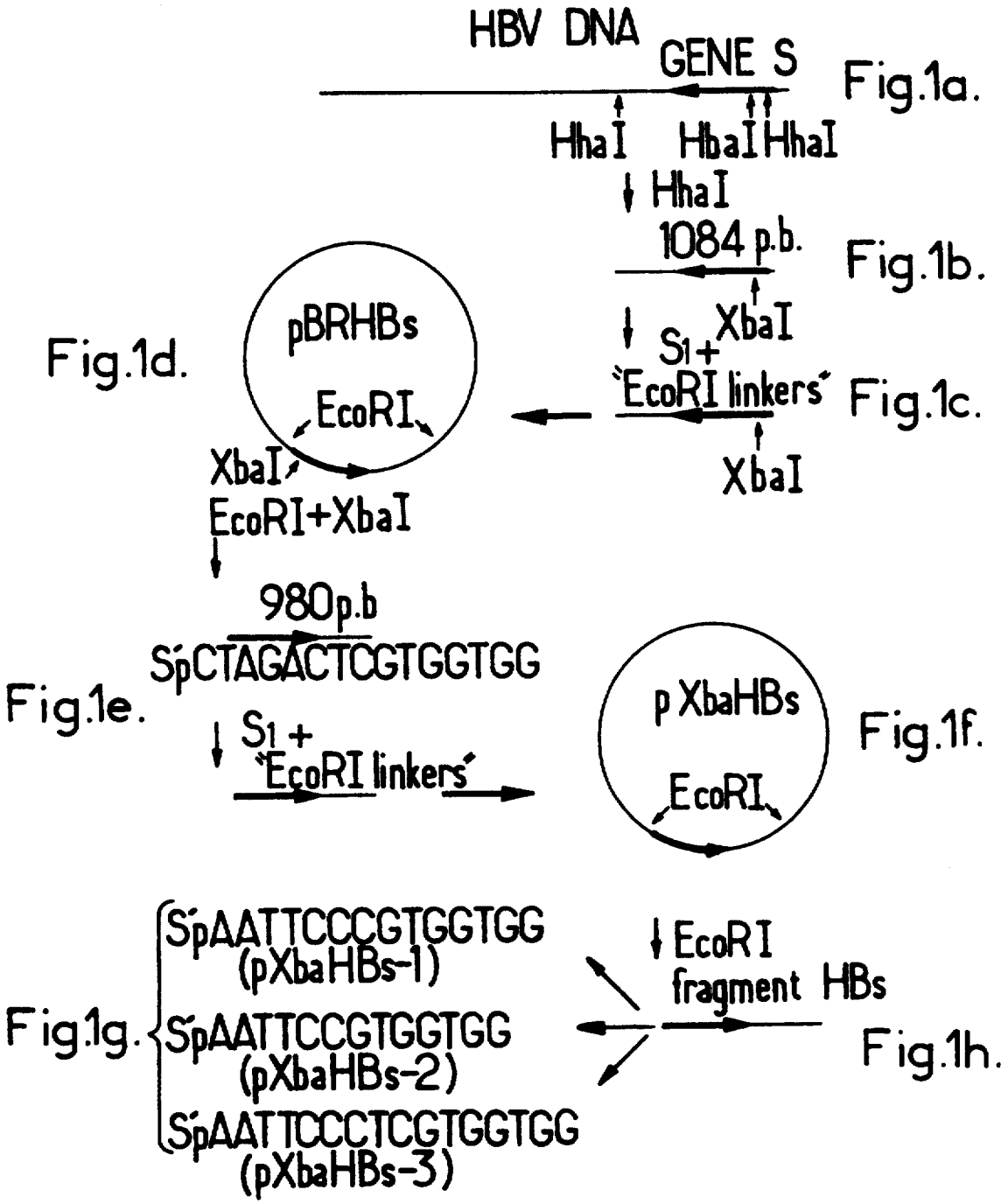
FIGS. 1a–1h illustrate diagramatically the steps in the manufacture of a vector plasmid type incorporating a fragment of HBV DNA.
Figures 2A, 2B, 2C:
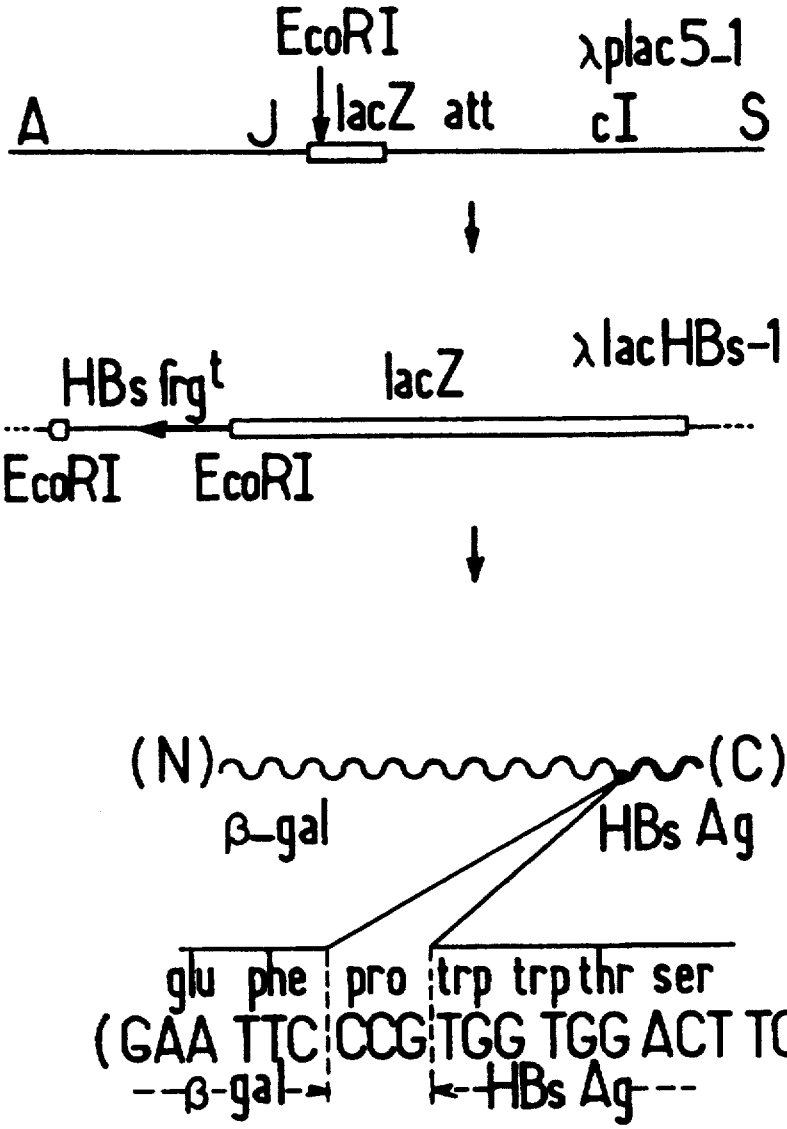
FIG. 2a is a diagramatic chart of a vector.
FIG. 2b is a diagramatic chart of FIG. 2a showing the modification introduced into its gene Z.
FIG. 2c shows a diagramatic structure of the hybrid polypeptide obtained as a result of the expression of the modified vector of FIG. 2b.

Other characteristics of the invention will appear also in the course of the description of preferred examples, in combination with the drawings in which:

- the FIGS. 1a and 1h illustrate diagrammatically the steps in the manufacture of a vector of the plasmid type incorporating a fragment of HBV DNA.
- FIGS. 2a to 2c illustrate diagrammatically the initial structures of the final vector used (FIG. 2a) of the modified vector obtained (FIG. 2b) and that of the hybrid protein resulting form the expression of this modified vector into E. coli. (FIG. 2c).

A—NUCLEOTIDE SEQUENCES

Products and methods used

The enzymes and chemical substances used

The restriction enzymes used: BamHI, HhaI, HincII, HaeIII, XbaI, MboI, HinfI, HpaII, XhoI, are those manufactured by BIOLABS. DNA-polymerase I of BOEHRINGER was used. The bacterial alkaline phosphatase and the polynucleotide-kinase were supplied by P. L. BIOCHEMICALS. The chemical agents were the following:

- Dimethyl sulfate (ALDRICH),
- Hydrazine (EASTMAN KODAK),
- Acrylamide and bis-acrylamide (twice crystallized -SERVA),
- Dideoxy nucleotide triphosphates and deoxynucleotide triphosphates (P. L. BIOCHEMICALS),
- Piperidine (MERCK) redistilled in vacuo

Preparation of DAN HBV

The whole HBV genome (sub-type ayw) was closed in E. coli by bringing into play the single EcoRI restriction site of the λgt. WES. λB vector (14). The cloned DNA is called below "Eco HBV DNA".

The recombinant bacteriophage was grown in a Petri dish on Agar and the desired DNA was extracted in manner known in itself. After digestion of the DNA by the EcoRI restriction enzyme, the Eco HBV DNA sequence was purified by ultracentrifugation, in a sucrose gradient, according to the technique described in the bibliographical references (16, 17).

Preparation of 5′ $^{32}$P labelled DNA fragments 10 to 20 picomoles of Eco HBV DNA were completely hydrolysed by the various restriction enzymes, under the conditions recommended by the manufacturer. The DNA fragments were dephosphorylated by alkaline phosphatase, the latter having then been inactivated by alkaline treatment. The DNA was then precipitated with ethanol, by the technique described in the article (18). After redissolving in a buffer based on spermidine, the DNA's were labelled at their 5′ ends with an ATP {λ$^{32}$P (3,000 Ci/mM manufactured by NEW ENGLAND NUCLEAR)} and with polynucleotide-kinase (according to the technique indicated in the article) (19).

The DNA restriction fragments were separated by electrophoresis on polyacrylamide gel, then eluted. The labelled ends were the subject of segregations by electrophoresis on polyacrylamide gel in manner known in itself, after restriction with another enzyme or by denaturation of the DNA fragments of the type concerned.

Determination of the structure of the nucleotide sequences of DNA

The primary structure of the double strand or single strand DNA fragments was determined essentially according to the technique described by MAXAM and GILBERT (19). Recourse was also had to the method of terminal chain inhibiters described by SANGER and al. (20) and adapted by MAAT and SMITH (21), as regards the double strand fragments labelled at one of their 5′ ends.

The chemical and enzymatic reaction products were analysed by electrophoresis in gels of acrylamide in sequence at 8, 16 or 25%, of 1 mm thickness.

Analytical techniques and results

In order to determine whether the HBV genome is capable of coding the polypeptides I and II, all the HaeIII fragments (HaeIII restriction sites of the HBV genome shown in FIG. 1 by small arrows) were labelled at their 5′ ends. Substantial portions of their primary structures were determined by the method of MAXAM and GILBERT. The nucleotide sequences capable of coding the proximal and terminal amino-acid sequences of the polypeptides I and II were localized in the HaeIII E and HaeIIIFF fragments, previously localized on the restriction map of the HBV genome-according to the technique described in the reference (17). It is these nucleotide sequences which have been considered as consisting of the ends of the "gene S" occupying themselves the positions 73.6 and 95.1 with respect to the EcoRI restriction site (FIG. 1) for the reasons already indicated.

The nucelotide sequence between these two positions has been analysed by resorting to known chemical techniques, notably by the chemical degradation method with hydrazine dimethyl sulfate and the method of chain termination. Recourse was had, among the various chemical reactions proposed by MAXAM and GILBERT to a partial depurination by formic acid and with cleavage by piperidine, methods which give equal intensity bands on autoradiograms for the fragments terminated by guanine and an adenine. Reactions with hydrazine followed by cleavage with piperidine were also used to obtain bands of equal intensity, for the cytosine and thymidine nucleotides: electrophoretic fractionation of the products of these two reactions gives for all the bases a spot in one or other of the gel columns used. This procedure facilitates the reading of the autoradiogram of the gel. The reaction with hydrazine in the presence of sodium chloride specific for cytosine enables this nucleotide to be distinguished from thymidine and the reaction with dimethyl sulfate followed by cleavage by piperidine, specific for guanine, enables the latter nucleotide to be distinguished from adenine.

In order to ensure the greatest possible degree of accuracy, distinct sequences of nucleotides forming different mutually straddling fragments were produced by hydrolysis of Eco HBV DNA by various restriction enzymes:

BamHi, HinfI, HpaII, HaeIII and HincII.

In this way the analysis of each of the restriction sites used as starting points of the first fragments studied was confirmed by analysis of the separate fragments in which the restriction sites of the first fragments are comprised between the new ends of these separate fragments.

The "gene S" shown in FIGS. 3A, 3B, 3C, which commence by the initiation codon ATG, comprises 227 triplets, including a stop codon TAA. The three codons corresponding to the 3 amino acids of the terminal carboxy end of the corresponding polypeptide are situated in the same reading frame, immediately before the stop codon TAA. One of the two other reading frames (respectively offset to the preceding one by 1 and 2 nucleotides) is also devoid of a stop codon, but codes quite a different protein from the polypeptides I and II above-mentioned. The third reading frame comprises 10 stop codons (5 TAG, 4TGA, 1TAA). On the other DNA strand, the three reading frames are respectively closed by 11, 11, and 6 stop condons distributed along the DNA sequence.

As has already been indicated above, the complete translation of the genetic information starting by the initiation codon ATG leads to a theoretical polypeptide of 226 amino-acids corresponding to a molecular weight of 25,422 daltons.

It is interesting to stress that the nucleotide sequence corresponding to the "gene S" should normally be read entirely in the course of translation.

Equally to be regarded as part of the invention are the nucleotide chains of the above-described "gene S" type, which comprises small additional sequences which can contain up to one hundred nucleotides or which on the contrary may be devoid thereof, without however the corresponding genetic information being altered (22, 23).

The various fragments of the invention which have been defined above may be obtained from the so-called Eco HBV DNA DNA sequence, by resorting to the corresponding restriction enzymes and to the known fractionation techniques of DNA fragments, notably on a polyacrylamide gel and applying their migrations over distances which are a function of their molecular weights. Thus it is possible for example to obtain the fragment of which one of the ends is bounded by an EcoRI site and the other by an AvaIII site by operating an Eco HBV DNA restriction by the AvaIII enzyme, the desired fragment consisting of the smallest fragment obtained (a single AvaIII site in Eco HBV DNA).

The fragment bounded by the opposite ends EcoRI and HhaI is obtained by hydrolysis of Eco HBV DNA by EcoRI first, then by partial hydrolysis by the restriction enzyme HhaI. Among the restriction products was then recovered that which contains the AvaIII site.

These restriction techniques have obviously only been proposed by way of example, it being well understood that the specialist is himself able to determine the order of treatment with restriction enzymes to isolate, starting notably with Eco HBV DNA, the fragments having useful restriction ends.

Insofar as it may be useful, it is recalled that these restriction operations can be carried out in a 10 mM Tris buffer at pH 7.8; 6 mM $MgCl_2$;6 mM $\beta$-mercaptoethanol, the same medium containing in addition preferably 50 mM of NaCl when EcoRI is used.

As has already been said, the invention relates to the use of the DNA fragments described as a probe enabling diagnosis of the presence in a serum of Dane particles or particles derived from the preceding one, bearing a DNA capable of coding an immunogen protein characteristic of hepatitis B.

The DNA according to the invention can also be incorporated in a vector enabling, on condition that the incorporation has been carried out in phase, the expression of this DNA into a bacterium or other microorganism, or into eucaryotic cells.

B—VECTORS CONTAINING A NUCLEOTIDE SEQUENCE OF HBs ANTIGEN

Construction of a λlac HBs-1 recombinant bacteriophage

The products at the level of the different stages of this construction are indicated in FIGS. 1a and 1h. They are also indicated by the numbers 1a to 1h.

In FIG. 1a are indicated the positions of the "gene S" and of certain restriction enzyme sites.

After treatment of DNA+HBV with HhaI restriction enzyme, a DNA fragment (1b) was separated containing 1,084 pairs of bases, and more particularly the whole of the "gene S" by electrophoresis on agarose gel and electroelution (FIG. 1b). There was prepared from this sub-fragment, treated previously by endonuclease S1, a sub-fragment, (1c) (FIG. 1c), resulting from the elongation of the sub-fragment (1b) at its ends, by DNA elements named "EcoRI linkers" of the formula:

5' GGAATTCC

CCTTAAGG 3'

The fragment obtained was, after formation of the EcoRI cohesive ends, cloned in the plasmid pBR322.

The plasmid obtained named below pBRHBs (FIG. 1d), only contains a single restriction site Xbal located close to the head of the "gene S".

By digestion of the pBRHBs recombinant plasmid with a mixture of EcoRI and XbaI enzymes, a DNA fragment comprising approximately 980 pairs of bases and including the major part of the "gene S" (FIG. 1e) was produced. This fragment was separated and purified by electrophoresis on agarose gel. The fragment obtained was again treated with S1 endonuclease, then again provided with EcoRI ends by means of the above-said "EcoRI linkers" then subjected to treatment with EcoRI endonuclease to reform the corresponding cohesive ends. The fragment of FIG. 1e which comprises about 980 pairs of bases is then inserted by in vitro fusion into the EcoRI site of the plasmid pBR322, to form the plasmid pXbaHBs (FIG. 1f). This plasmid was cloned in the usual manner like the plasmid pBR322.

Several clones were obtained.

There were extracted and purified, after treatment with EcoRI in DNA's of three of these clones, pXbaHBs-1, pXbaHBs-2, pXbaHBs-3 (FIG. 1g), the fragments called below "HBs fragments"(FIG. 1h).

The nucleotide sequences of the ends of the above-said fragments (normally obtained inside the "gene S") were determined by resorting to the procedure described by MAXAM and GILBERT (Proc. Nat. Acad. Sci. USA 74, 560–564 (1977). These determinations have shown that the sequences of the nucleotides of the terminal ends, corresponding to the "gene S" were not identical in the three clones (FIG. 1g), the differences are apparently due to heterogeneities produced in the course of digestion with the S1 endonuclease.

The two fragments coming from the pXbaHBs-1 and pXbaHBs-2 were inserted by fusion in vitro into the bacteriophage genome λplac 5-1 (21), which had only a single EcoRI site situated close to the end of the lac Z gene. Due to the fact of the reading frame of the lac Z gene, such as can be produced form the amino-acid sequence of β-galactosidase (23), it is observed—and experiment confirms it—that the insertion of the HBs fragment of pXbaHBs-1 into the EcoRI site of the lac Z gene of λplac 5-1 must lead to the preservation of the adequate reading phase of the "gene S". On the contrary, the insertion of the HBs fragment of pXbaHBs-2 should be revealed as not capable of being inserted into the preceding vector with preservation of the suitable reading frame. It has nonetheless been used as a control in later experiments.

These operations were carried out by resorting to known techniques. In particular the "HBs fragments" of pXbaHBs-1, pXbaHBs-2 were inserted by means of a ligase into the DNA of λplac 5-1 which had previously been cleaved by EcoRI. The mixtures of DNA fragments obtained where then used to transfect the strain C600RecBC rk−mk− of E. coli. The bacteriophage clones become lac− due to the fact of the insertion of the HBs fragments into the EcoRI sites of the lac Z gene were amplified and purified by the method described in (21).

The DNA's of the different bacteriophages were extracted and the orientations of the DNA fragments inserted determined by electrophoretic analysis of their BamHI restriction fragments. It was thus possible to determine that two phages called lacHBs-1 and lacHBs-2 corresponding to the pXbaHBs-1 and pXbaHBs-2 plasmid contained a correctly oriented HBs fragment.

FIG. 2a is a diagrammatic chart of the plac 5-1 vector before its modification by the HBs-1 fragment, coming from the pXbaHSs-1.

FIG. 2c is a diagrammatic chart of a portion iw this same vector showing the modification introduced into its gene Z by insertion into its EcoRI site of the above-said HBs-1 fragment.

FIG. 2c shows diagrammatically the structures of the hybrid polypeptide obtained as a result of the expression of the modified vector of FIG. 2b.

The expression was achieved by a transfection of strain of E. coli bacteria, notably of HfrΔlacX74.

The strains of E. coli, notably a strain of E. coli Hfr lac X74 were converted by plac 5-1 and λlacHBs-1 and λlac HBs-2 respectively. After cultivation, the cells were lysed and the lysates obtained analysed by electrophoresis on SDS polyacrylamide gel (24) and the proteins were detected by dyeing with coomassie blue. The presence of a stronger band among the expression products of λplac 5-1 was detected at the level of the position corresponding, for a control, with that of βgalactosidase (molecular weight of 116 248) and of a separate band among the expression products of λlac HBs-1 (not present among the expression products of λlacHBs-2) corresponding to a novel protein having a molecular weight of the order of lac HBs-2) 135 000–141 000.

The proteins synthesized by the bacteria transfected both by λlacHBs-1 and by λplac 5-1 were labelled by ($^{35}S$) methionine. The contacting of these proteins with an anti-HBsAg serum and the production of an autoradiogram of the SDS polyacrylamide gel reveal the presence among the expression products of only λlacHBs-1 of a band to which there does not correspond an equivalent band among the expression products of the other vectors. This band disappeared specifically when immunoprecipitation was carried out in the presence of unlabelled HBsAg. There was also observed the same band among the λlacHBs-1 expression products, when immunoprecipitation was carried out with an antiserum with respect to β-galactosidase.

The presumed structure of the hybrid protein part obtained, at the level of fusion between the lac Z gene and the HBs-1 fragment results from FIG. 2c which shows the β-gal" fragment, corresponding to β-galactosidase (1,005 amino acids), the HBsAg fragment (192 amino acids), these fragments being separated by a prolyn amino acid, corresponding to a part of "EcoRI linker" contained in the λlacHBs-1 vector.

C—PROCESS FOR MANUFACTURE OF AN IMMUNOGEN MOLECULE APPLYING THE VECTOR ACCORDING TO THE INVENTION

The invention can consequently permit the production of a protein of a molecular weight lower than the aboveindicated polypeptides I or II, endowed with the same immunogen properties.

The results show that E. coli, or any other suitable micro-organism, such as a bacterium or a eucaryotic cell culture, can be infected by λlacHBs-1 and synthesize a protein having a molecular weight of the order of 138,000 possessing determinants antigenic both of HBsAg and of β-galactosidase. This molecule is representative of the hybrid polypeptides which can be obtained by the process according to the invention, in which HBsAg is connected to a support protein (resulting from the partial or total substitution of the β-galactosidase fragment), these hybrids possessing nonetheless the antigen properties of HBsAg. These novel molecules are useful for the production of vaccines active against viral hepatitis B.

As is self-evident, and as emerges already from the foregoing, the invention is in no way limited to those of its types of application and embodiments which have been more especially envisaged; it encompasses, on the contrary, all modifications.

Appended to this description is a bibliography, in particular of the references which have been cited within the scope of the present description.

REFERENCES

1—Blumberg, B. S. (1977) Science 197, 17-25

2—Dane D. S., Cameron C. H., and Brigss M. (1970)Lancet 1, 695-698

3—Who Technical Report series, number 602 (1976)

4—Summers J., O'Connel A., and Millman I. (1975) Proc. Nat. Acad. Sci. USA 72, 4 597-4 601

5—Hruska J. F., Clayton E. A., Rubenstein J. L. R. and Robinson W. S. (1977) J. Virol. 21 666-682.

6—Landers T. A., Greenberg H. B. and Robinson W. S. (1977) J. Virol. 23, 368-376

7—Charnay P., Pourcel C., Louise A., Fritsch A. and Tiollais P. (1979) Proc. Nat. Acad. Sci. USA, 76 2,222-2,226

8—Dreesman G. R., Hollinger F. B. Surians J. R., Fujioka R. B., Brunschwig J. P. and Melnick J. L. (1972) J. Virol. 10, 469-476

9—Gerin J. L. (1974) in Mechanisms of virus disease Ed. W. S. Robinson, C. R. Fox pp 215-24 Menlo Park: W. A. Benjamin 10—Dreesman G. R. Chairez R., Suarez M., Hollinger F. B. Courtney R. J. and Melnick J. L. (1975) J. Virol. 16, 508-515

11—Shih J. W. and Gerin J. L. (1977) J. Virol. 21, 1,219-1,222

12—Peterson D. L., Roberts I. M. and Vyas G. N. (1977) Proc. Nat. Acad. Sci. USA 74, 1,530-1,534

13—Peterson D. L., Chien D. Y., Vyas G. N., Nitecki D. and Bond H. (1978) in Viral Hepatitis, Ed. G. Vyas. S. Cohen and R. Schmid. The Franklin Institute Press, Philadelphia, 569-573

14—Fritsch A., Pourcel C., Charnay P. and Tiollais P. (1978) C. R. Acad Sc. Paris 287, 1,453-1,456

15—Burrell C. J. Mackay P., Greenaway P. J., Hofschneider P. H. and Murray K. (1979) Nature 279 43-47

16—Tiollais P., Perricaudet M., Pettersson U. and Philipson L. (1976) Gène 1, 49-63

17—Hérissé J., Courtois G., and Galibert F. (1978) Gène 4, 279-294

18—Kroeker W. D. and Laskowski M. S. R. (1977) Anal. Biochem 79, 63-72

19—Maxam A. M. and Gilbert W. (1977) Proc. Nat. Acad. Sci. USA 74, 560-564

20—Sanger F., Nicklen S. and Coulson A. R. (1977) Proc. Nat. Acad. Sci. USA 74, 5 463-5 467

21—Maat J. and Smith A. J. W. (1978) Nucleic Acid. Res. 5, 4,537-4,545

22—Berget S. M., Moore C. and Sharp P. A. (1977) Proc. Nat. Acad. Sci. USA 74, 3,171-3,175

23—Chow L. T., Gelinas R. E., Broker T. R., and Roberts J. (1977), Cell 12, 1-8

24—Shiraishi H., Kohama T., Shirachi R. and Ishida N. (1977) J. Gen. Virol. 36, 207-210

25—Struck D. K., Lennarz W. J., and Brew K. (1978) J. Biol. Chem. 253, 5,786-5,794

26—Reddy V. B., Thimmappaya B., Dhar R., Subramanian K. N., Zain B. S., Pan J., Celma C. L. and Weissman S. M. (1978) Science 200, 494-502

27—Fiers W., Contreras R., Hargeman G., Rogiers R., Van de Voorde A., Van Henverswyn H., Van Herreweghe J., Volchaerts G. and Ysebaert M. (1978) Nature 273, 113-117

28—Sanger F., Air G. M., Barrell B. G., Brown N. L., Coulson A. R., Fiddes J. C., Hutchison III C. A., Slocombe P. M. and Smith M. (1977) Nature 265, 687-691

29—Barrell B. G., Shaw D. C., Walker J. E., Northrop F. D., Godson G. N. and Fiddes J. C. (1978) Biochem. Soc. Trans. 6, 63-67

30—Szmuness W., Am. J. Path. 81, 629-649 (1975)

31—Sninsky J. J., Siddiqui A., Robinson W. S. and Cohen S. N., Nature 279, 346-348 (1979)

32—Valenzuela P. et al., Nature 280, 815-819 (1979)

33—Charnay P. et al., Nucl. Acids Res. 7, 335-346 (1979)

34—Galibert F., Mandart E., Fitoussi F., Tiollais P. and Charnay P., Nature 281, 646-650 (1979)

35—Pasek M. et al., Nature 282, 575-579 (1979)

36—Vyas G. N., Williams E. W., Klaus G. G. B. and Bond H. J. Immunol. 108 1,114-1,118 (1972)

37—Holinger F. B., Dreesman G. R., Sanchez Y., Cabral G., and Melnick J. L., in Virol Hepatitis (Ed. Vyas G. N. Cohen S. N. and Schmid R.) Franklin Institute, Philadelphia, (1978)

38—Purcell R. H., and Gerin J. L., Am. J. Med. Sci. 270, 395-399 (1975)

39—Hillerman M. R. et al., Am. J. Med. Sci. 270, 401-404 (1975)

40—Maupas P., Coursaget P., Goudeau A. and Drucker J., Lancet 1, 1,367-1,370 (1976)

41—Emtage J. S. et al., Nature 283, 171-174 (1980)

42—Itakura K. et al., Science 198, 1,056-1,063 (1977)

43—Goeddel D. V. et al., Prox. Nat. Acad. Sci. USA 76, 106-110 (1979)

44—Pourcel C., Marchal C., Louise A., Fritsch A. and Tiollais P., Molec. Gen. Genet, 170, 161-169 (1979).

45—Bolivar F. et al., Gene 2, 95-113 (1977)

46—Fowler A. V. and Zabin I., Proc. Natl. Acad. Sci. USA 74, 1,507-1,510 (1977)

47—Laemmli U. K., Nature 227, 680-685 (1970)

48—Burgess R. R., J. Biol. Chem. 244, 6,168-6,176 (1969)

49—Bonner W. M. and Laskey R. A., Eur. J. Biochem. 46,83-88 (1974)

50—Laskey R. A. and Mills A. D., Eur. J. Biochem. 56, 335-341 (1975)

51—Iwakura Y., Ito K. and Ishihama A., Molec. Gen. Genet. 133, 1-23 (1974)

52—Talwai G. P., et al., Proc. Nat. Acad. Sci. USA 73, 218-222 (1976)

We claim:

[1. A peptide which comprises the sequence: Alanine-Glutamine-Glycine-Threonine-Serine, wherein the alanine end is N-terminal and the serine end is C-terminal.]

[2. A peptide which comprises the sequence: Threonine-Alanine-Glutamine-Glycine-Threonine-Serine, wherein the threonine end is N-terminal and the serine end is C-terminal.]

[3. A peptide which comprises the sequence: Threonine-Threonine-Alanine-Glutamine-Glycine-Threonine-Serine, wherein the threonine end is N-terminal and the serine end is C-terminal.]

[4. A peptide which comprises the amino acid sequence of FIG. 5 starting with serine (number 113) and ending with tryptophan (number 165).]

[5. The peptide of claim 4 which comprises within the peptide the amino acid sequence: Alanine-Glutamine-Glycine-Threonine-Serine.]

[6. The peptide of claim 3 which comprises within the peptide the amino acid sequence: Threonine-Alanine-Glutamine-Glycine-Threonine-Serine.]

[7. The peptide of claim 4 which comprises within the peptide the amino acid sequence: Threonine-Threonine-Alanine-Glutamine-Glycine-Threonine-Serine.]

[8. An immunogenic peptide sequence which comprises the amino acids shown in FIGS. 3A, 3B, and 3C numbering not less than 5 amino acids and not more than 226 amino acids which peptide induces in vivo the production of active antibodies with respect to the hepatitis B virus.]

[9. The immunogenic peptide sequence which comprises the amino acids shown in FIG. 6 numbering not less than 5 amino acids and not more than 53 amino acids, which peptide induces in vivo the production of active antibodies with respect to the hepatitis B virus.]

[10. A pharmaceutical composition comprising an effective amount of the peptides of claims 1, 2, 3, 4, 5, 6 or 7, wherein composition includes in vivo production of antibodies, the hepatitis B-virus, and a pharmaceutically acceptable carrier.]

*11. A portion of surface antigen protein of hepatitis B virus, wherein said portion consists essentially of a polypeptide having the sequence: Alanine-Glutamine-Glycine-Threonine-Serine.*

*12. A portion of surface antigen protein of hepatitis B virus, wherein said portion consists essentially of a polypeptide having the sequence: Threonine-Alanine-Glutamine-Glycine-Threonine-Serine.*

*13. A portion of surface antigen protein of hepatitis B virus, wherein said portion consists essentially of a polypeptide having the sequence: Threonine-Threonine-Alanine-Glutamine-Glycine-Threonine-Serine.*

* * * * *